US00PP21735P3

(12) United States Plant Patent
Patel

(10) Patent No.: US PP21,735 P3
(45) Date of Patent: Mar. 1, 2011

(54) BLUEBERRY VARIETY NAMED 'OCEAN BLUE'

(50) Latin Name: *Vaccinium virgatum*
Varietal Denomination: Ocean Blue

(75) Inventor: Narandra Patel, Hamilton (NZ)

(73) Assignee: The New Zealand Institute for Pland and Food Research Limited, Auckland (NZ)

( * ) Notice: Subject to any disclaimer, the term of this patent is extended or adjusted under 35 U.S.C. 154(b) by 0 days.

(21) Appl. No.: 12/590,311

(22) Filed: Nov. 5, 2009

(65) Prior Publication Data

US 2010/0115679 P1 May 6, 2010

Related U.S. Application Data

(60) Provisional application No. 61/198,544, filed on Nov. 6, 2008.

(51) Int. Cl.
*A01H 5/00* (2006.01)

(52) U.S. Cl. ..... Plt./157

(58) Field of Classification Search ..... Plt./157

See application file for complete search history.

*Primary Examiner*—Annette H Para
(74) *Attorney, Agent, or Firm*—Greenlee Sullivan PC

(57) ABSTRACT

A new and distinct rabbiteye blueberry variety is described. The variety results from selection among a population of seedlings derived from crossing the blueberry varieties known as 'Centurion' (not patented) and 'Rahi' (not patented). The fruit of this new variety has an outstanding fruit quality with little grittiness, medium to good firmness and appears suitable for the mid season fresh fruit market and has been named 'Ocean Blue'.

7 Drawing Sheets

Genus and species of plant named: *Vaccinium virgatum.*
Variety denomination: Ocean Blue.

BACKGROUND OF THE INVENTION

This new rabbiteye blueberry variety was selected from a population of seedlings derived from crossing the blueberry varieties 'Centurion' (not patented) and 'Rahi' (not patented). The new variety was selected in February 2000 from among plants located on land at Ruakura, Hamilton, New Zealand, and was originally assigned the breeder code, F107. The new variety has since been named 'Ocean Blue'.

SUMMARY OF THE INVENTION

The fruit of this new variety has an outstanding fruit quality with little grittiness, medium to good firmness and appears suitable for the mid season fresh fruit market and has been named 'Ocean Blue'.

The new variety is characterised as follows:

Maturity period: Mid season, about the same window as 'Rahi' and 3 to 4 weeks earlier than 'Centra Blue' at the Ruakura, Hamilton, New Zealand.

Plant form and vigour: The plant is upright with medium to good vigour.

Yield: Medium to good.

Berry size: Medium, bigger than 'Centurion'.

Color: Medium blue.

Fruit bloom: Medium to poor.

Pedicel scar: Small.

Plant health: None of the main blueberry diseases have been recorded in this variety.

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

FIGS. 1A-1C shows the adult plant of 'Ocean Blue' planted in the field. FIG. 1A was taken in April 2008; FIG. 1B was taken in July 2008; and FIG. 1C was taken September 2009.

DETAILED DESCRIPTION

Figure 1A:
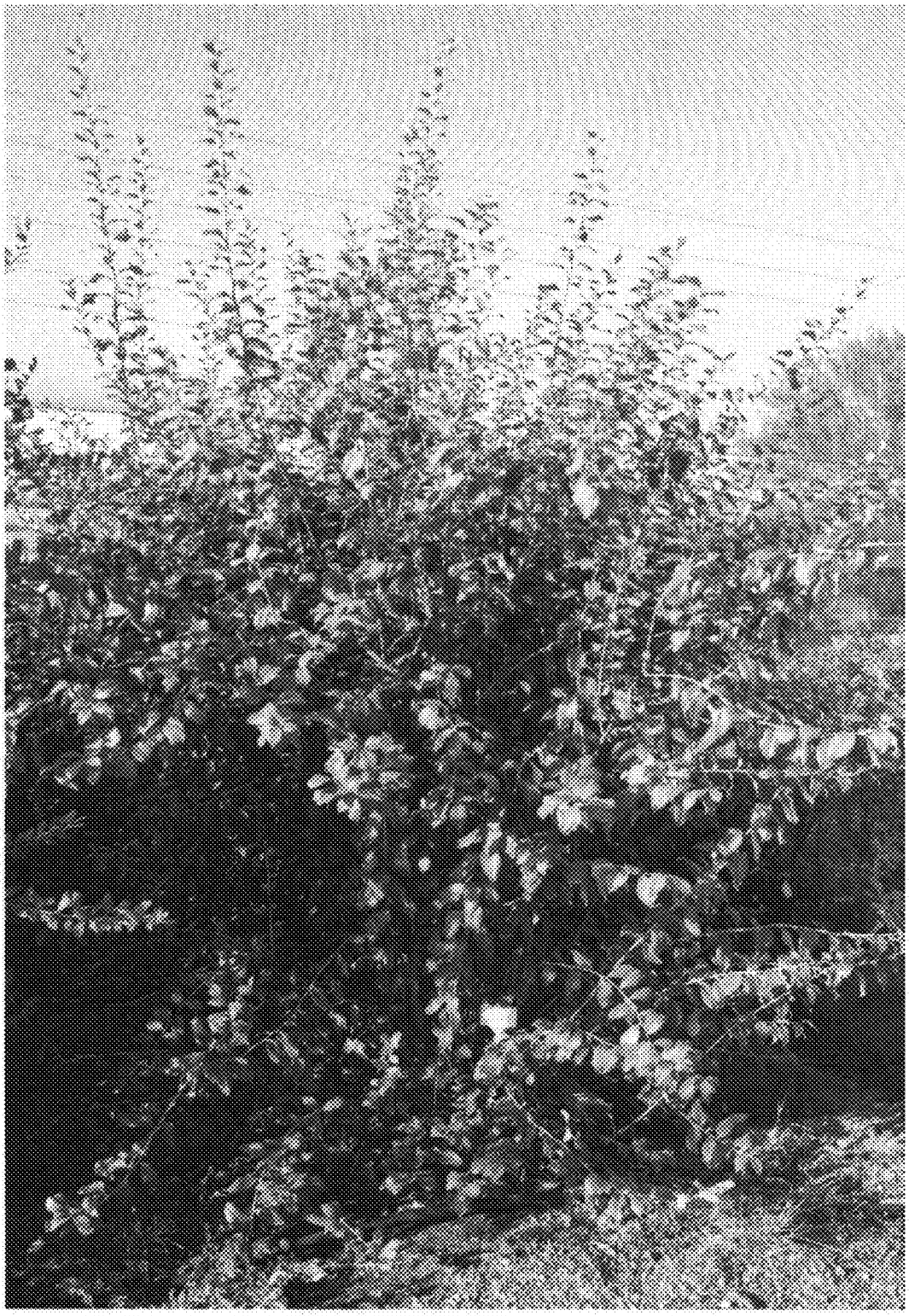
Figure 1B:
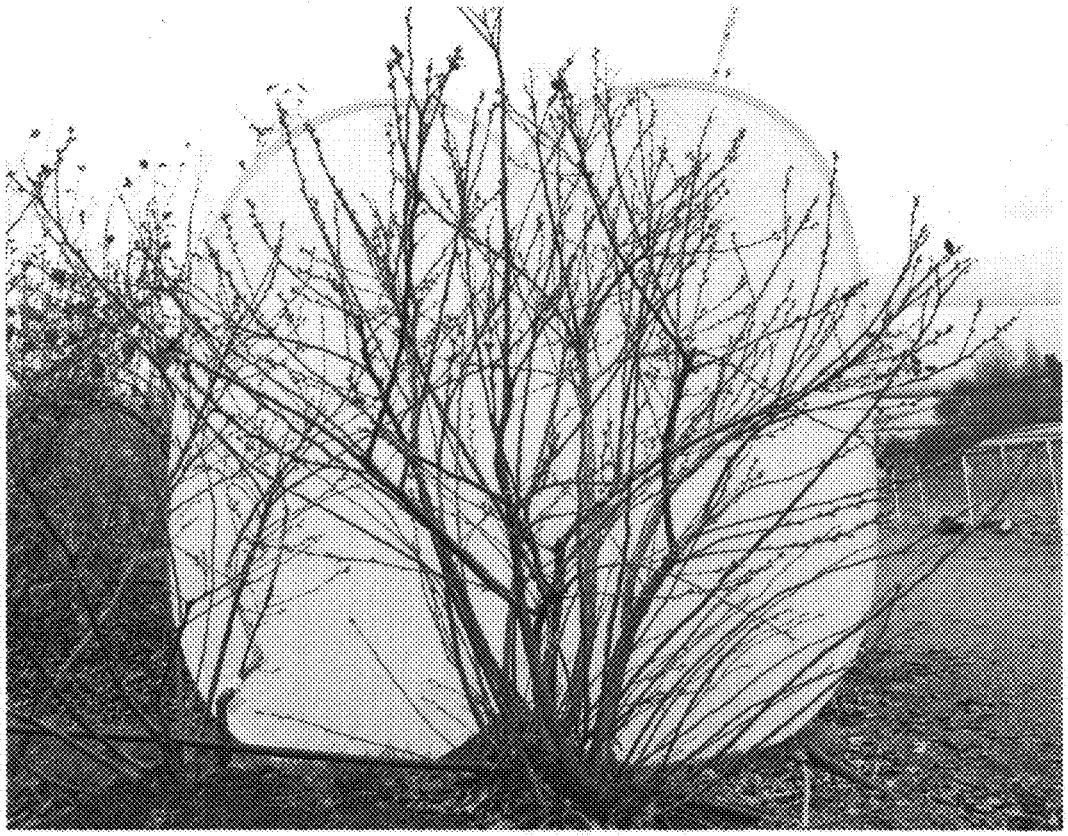
Figure 1C:
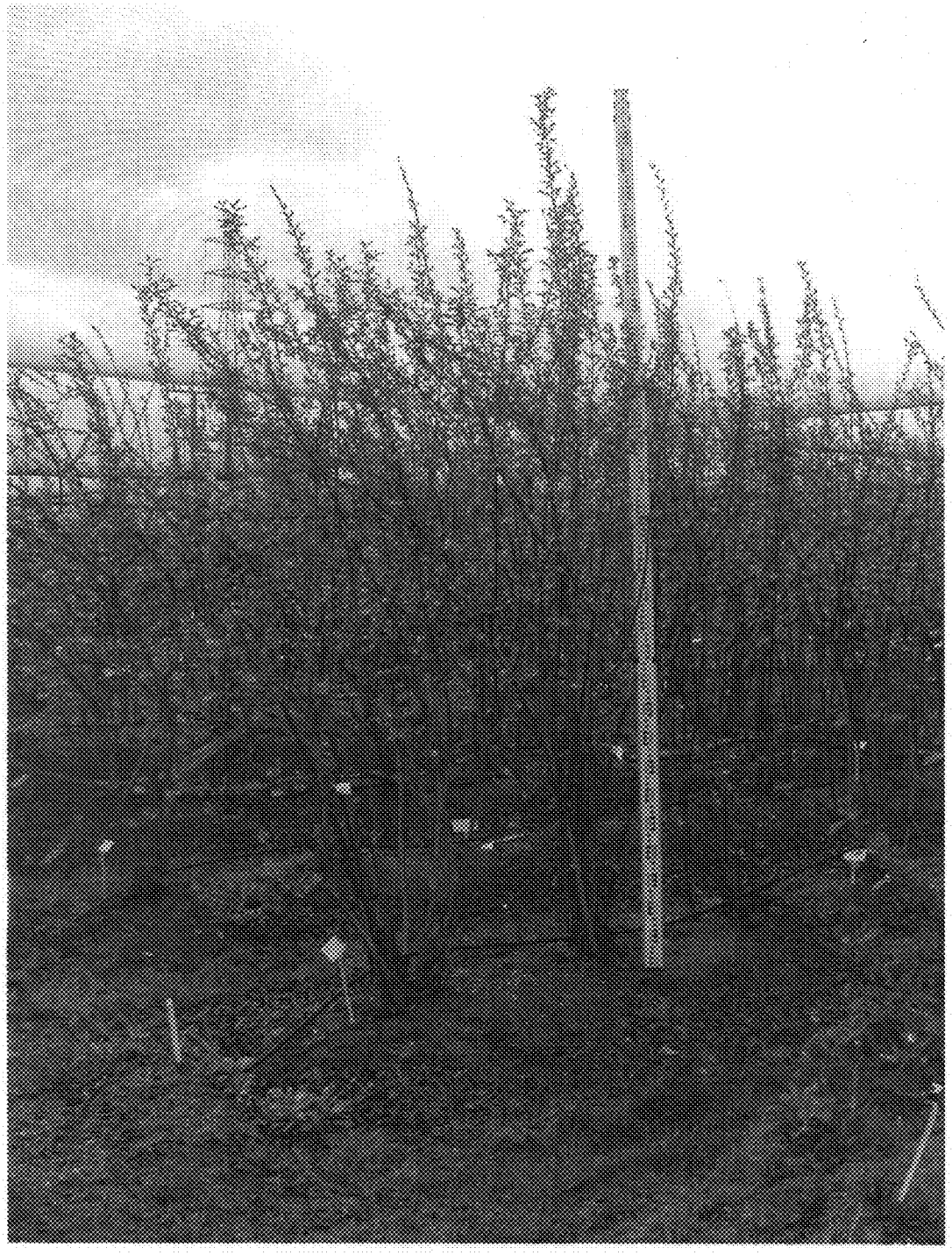
Figure 2:
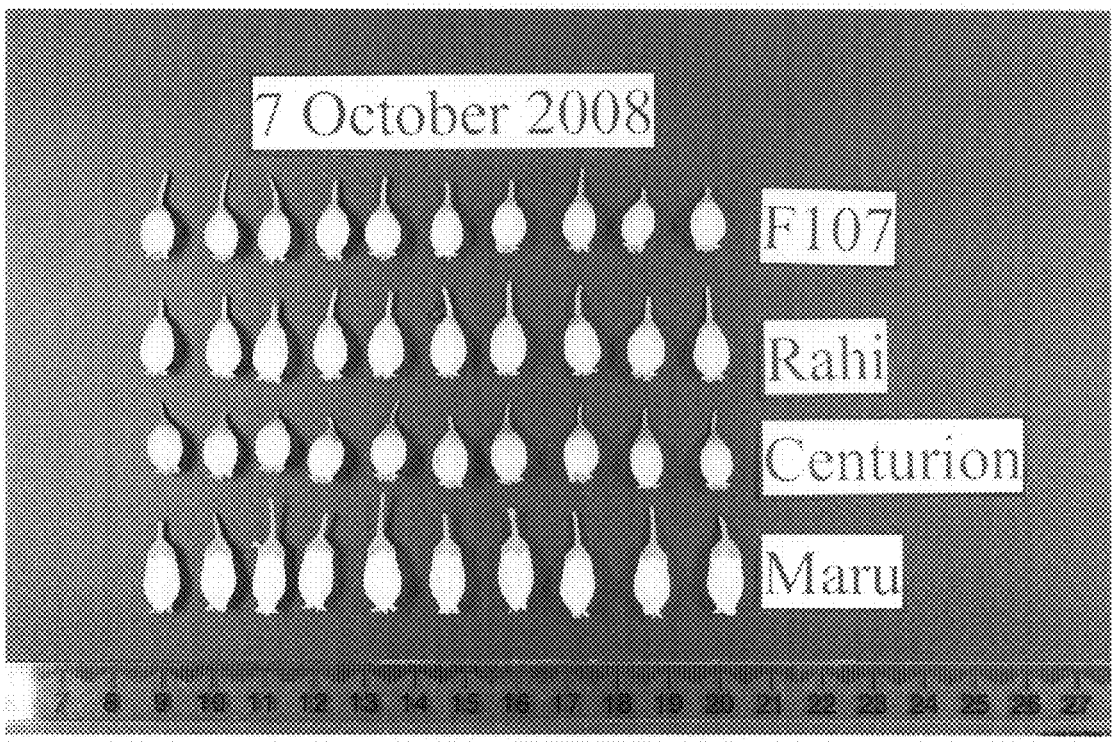
FIG. 2 shows the typical flowers collected from mature plants of 'Ocean Blue' (labeled in the figure as 'F107') in October 2008 and compared to the flowers of commercial varieties 'Rahi', 'Centurion' and 'Maru'.
Figure 3:
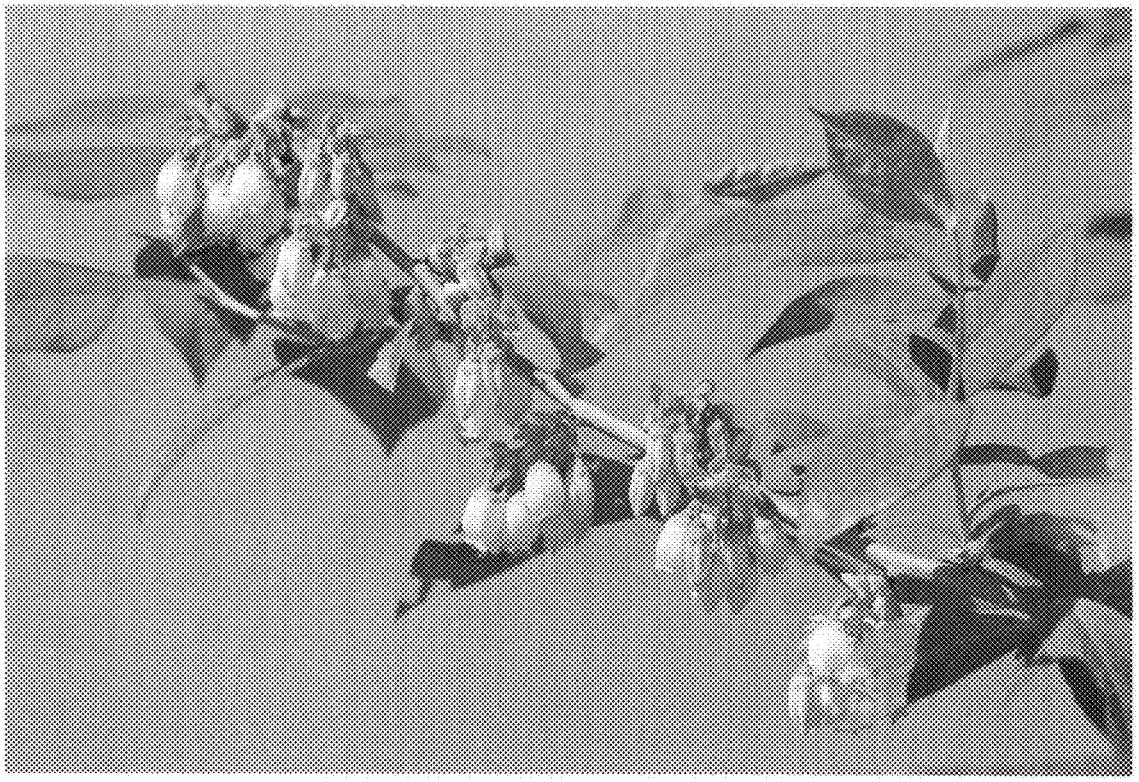
FIG. 3 shows a close up of the characteristic flowers coloration of 'Ocean Blue'.
Figure 4:
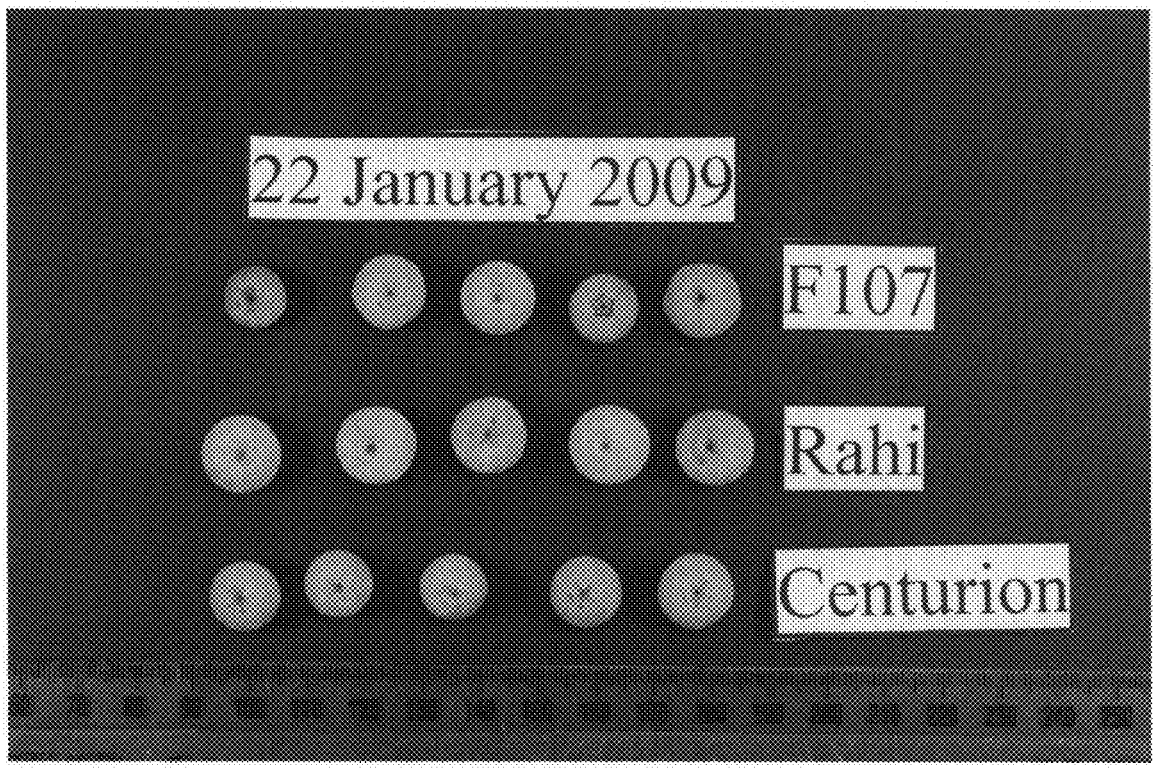
FIG. 4 shows the green fruit of 'Ocean Blue' (labeled in the figure as 'F107') compared with the fruit of parental plants 'Centurion' and 'Rahi'.
Figure 5A:
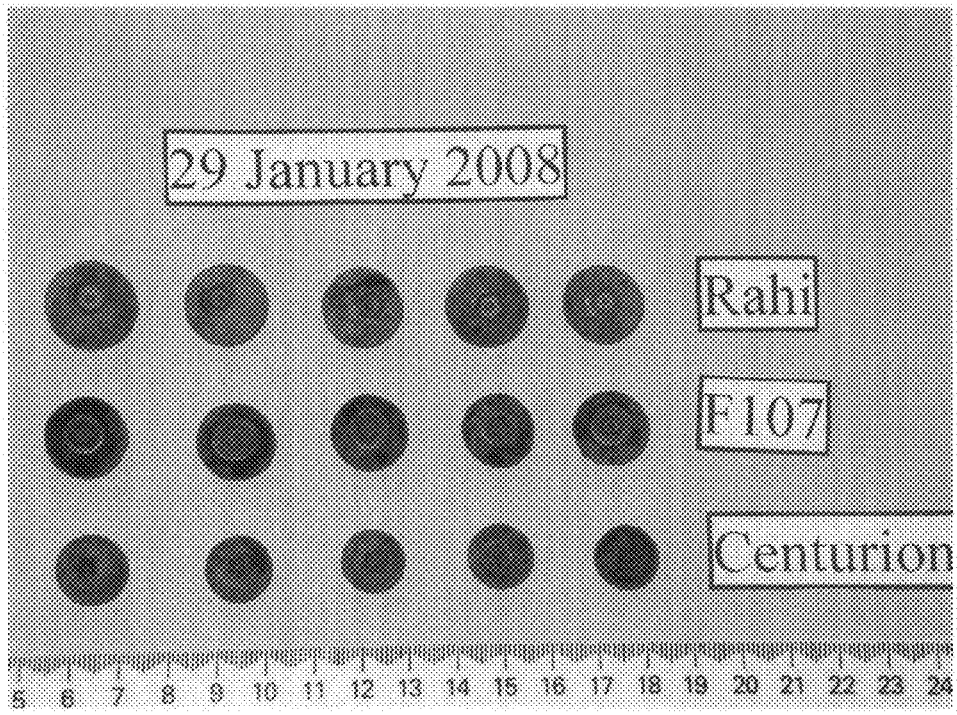
FIG. 5 shows typical fruit of 'Ocean Blue' (labeled in the figure as 'F107') compared with the fruit of parental plants 'Centurion' and 'Rahi'. Fruit is showed from the calyx (FIG. 5A) and from the pedicel scar (FIG. 5B).
Figure 5B:
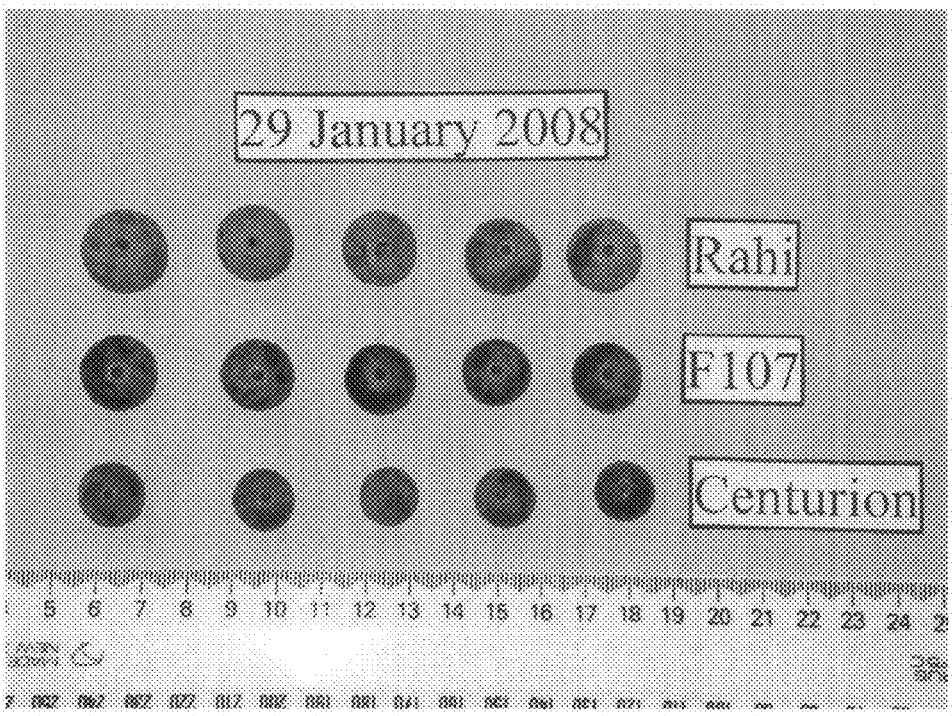

The observations, unless otherwise specified, were made in the 2008 and 2009 seasons on eight year old plants propagated and grown at Ruakura, Hamilton, New Zealand. All dimensions in millimeters, weights in grams (unless otherwise stated). Color terminology is in accordance with The Royal Horticultural Society Colour Charts 2001 edition.

Plant and foliage

This hexaploid plant is generally upright in habit with medium to good vigour.

The mature leaf is lanceolate in shape and typically averages 63 mm in length and approximately 34 mm in width. The typical leaf size of 'Ocean Blue' is intermediate between 'Rahi' (76 mm in length and 39 mm in width) and 'Centurion' (58 mm in length, 35 mm in width). Generally the leaf margin has serrate margins, medium to little glossiness on the upper surface, and no glaucescence on the upper surface. Typically the petiole length averages 1.9 mm.

The color of the leaf is near Green 137A, similar to that of the parent 'Centurion' (near green 137A) and different from that of the parent 'Rahi' (near green 137D). The leaf vein color is near Yellow-Green 152A.

The color of mature dormant wood is near Yellow-Green 146B and C on the top side of the cane, similar to 'Rahi', and near Greyed-Purple 184B and C on the underside of the same cane, differing from that of the parent 'Centurion' (near Red-Purple 60B on the top side of the cane and near Yellow-Green 146B on the underside of the same cane).

Inflorescence

The average number of flower buds per shoot is 8, with an observed range of 5-18. The estimation of number of buds per shoot was made on the fruiting (terminal) sections of shoots; this section typically averaging 22 cm in length and the average total shoot length is 67 cm.

Flowers are generally clustered and the width of the typical flower averages 6.5 mm, similar to that of the parents 'Centurion' (averaging 6.5 mm) and 'Rahi' (averaging 6.7 mm). The background color of the petals on fully open mature flowers is near White N155D and occasionally flowers have anthocyanin coloration of the petals near Red-Purple 69A and D. Observations indicate that flowers of the parents 'Centurion' and 'Rahi' are near White 155C with no anthocyanin coloration.

Fruit

The fruit is of medium size under New Zealand growing conditions, averaging approximately 1.5 g. Observations indicate fruit size is intermediate between that of the parents 'Centurion' and 'Rahi' (averaging 1.4 g and 1.7 g respectively).

The diameter of fruit of 'Ocean Blue' averages approximately 14 mm (observed range 12-15 mm) under New Zealand growing conditions, intermediate between the fruit diameter of the parents 'Centurion' and 'Rahi' (averaging 13.7 mm and 15.3 mm respectively).

Unripe fruit is green, within the range near Yellow-Green 145A similar to the green fruit color of 'Centurion' and 'Rahi'.

Ripe fruit of 'Ocean Blue' has a medium to poor bloom. Fruit color with the bloom intact is near Blue 103D, differing from that of the variety 'Centurion' (near Blue 100C) and 'Rahi' (near Violet-Blue 98C). The skin color of the fruit of the variety 'Ocean Blue' when bloom is completely removed is near Black 202A.

Observations indicate the pedicel scar of fruit of 'Ocean Blue' is small, approximately 1.4 mm in diameter, similar to that of 'Rahi' (averaging 1.5 mm) although larger than those measured in fruit of the parental parent 'Centurion' which were very small (1.1 mm). The scar is generally dry.

The fruit sweetness is high and the Brix level averaged 13.7%, similar to 'Rahi' (13.9%) and lower than 'Centurion' (averaging 14.9%).

The fruit acidity measured as titratable acidity (%) averaged 0.37 (observed range 0.3-0.5%), similar to 'Centurion' (0.5%). Fruit is generally firm, averaging 230 g/mm (observed range 190-260 g/mm), intermediate between that of 'Rahi' (averaging 210 g/mm) and 'Centurion' (245 g/mm).

Yield is medium to good, averaging over 4.5 Kg per adult plant under New Zealand growing conditions. Seed size is approximately 1.64 mm, with an average number of seeds per fruit of 14 (observed range approximately 3-42).

Events

According to observations the time of vegetative bud burst was around the 14 August, about two weeks earlier than the parents 'Centurion' and 'Rahi'. Time of beginning flowering recorded in New Zealand in 2008 was around the 11 September, reaching an estimated 50% of the flowering around the 26 September, about one week earlier than 'Centurion'.

The fruit maturity period occurs in mid season, similar to 'Centurion' and 'Rahi'. In 2008 the timing of 50% of blue fruit on the bush was estimated for both 'Ocean Blue' and the parental plants as the 3 February.

Disease and pests

None of the main blueberry diseases have been recorded in this variety.

The invention claimed is:

1. A new and distinct Rabbiteye blueberry variety substantially as described in the specification and illustrations.

* * * * *